United States Patent
Ogawa et al.

(10) Patent No.: US 6,599,500 B1
(45) Date of Patent: Jul. 29, 2003

(54) COMMUNICATION DISRUPTANT AND COMMUNICATION DISRUPTION METHOD

(75) Inventors: Kinya Ogawa, Tokyo (JP); Masaomi Azuma, Tokyo (JP); Fumiaki Mochizuki, Niigata-ken (JP); Takehiko Fukumoto, Niigata-ken (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 09/297,638

(22) PCT Filed: Sep. 4, 1998

(86) PCT No.: PCT/JP98/03973

§ 371 (c)(1), (2), (4) Date: May 5, 1999

(87) PCT Pub. No.: WO99/12419

PCT Pub. Date: Mar. 18, 1999

(30) Foreign Application Priority Data

Sep. 5, 1997 (JP) .............................................. 9-240939

(51) Int. Cl.$^7$ .............................................. A01N 37/02
(52) U.S. Cl. ......................................... 424/84; 514/546
(58) Field of Search ............................. 424/84; 514/546

(56) References Cited

U.S. PATENT DOCUMENTS

| | | | | |
|---|---|---|---|---|
| 3,866,349 A | * | 2/1975 | Meijer et al. .................. | 424/84 |
| 5,725,849 A | | 3/1998 | Mochizuki et al. ........... | 424/84 |

FOREIGN PATENT DOCUMENTS

| | | |
|---|---|---|
| JP | 57009705 | 1/1982 |
| JP | 57-146703 | 9/1982 |
| JP | 57156403 | 9/1982 |
| JP | 2-212404 | 8/1990 |
| JP | 8-231305 | 9/1996 |

OTHER PUBLICATIONS

Witzgall, P., "Attraction of Cacoecimorpha pronubana male moths to synthetic sex pheromone blends in the wind tunnel," Journal of Chemical Ecology, vol. 16 (5), 1990, pp. 1507–1515.*

Ando, T. et al., "Multi–component sex attractants in systematic field tests of male Lepidoptera," Agricultural and Biological Chemistry, vol. 45(2), 1981, pp. 487–495.*

* cited by examiner

*Primary Examiner*—John Pak
(74) *Attorney, Agent, or Firm*—Burns, Doane, Swecker & Mathis, L.L.P.

(57) ABSTRACT

When a communication disruptant containing (Z)-11-tetradecen-1-yl acetate as the only active ingredient is continually used for a period of 5 to 10 years, a phenomenon has been observed in which its communication-disrupting effect on insect pests, particularly of the family Tortricidae, living in the field or the like through successive generations is reduced. Accordingly, it is eagerly desired to develop a new communication disruptant which is also effective for such fields where the communication-disrupting effect (on insect pests, particularly of the family Tortricidae, living there through successive generations) has been reduced. The present invention provides, for use in the control of insect pests having (Z)-11-tetradecen-1-yl acetate contained in their sex pheromone, a communication disruptant containing (Z)-11-tetradecen-1-yl acetate and the maximum component in the composition of the sex pheromone excepting (Z)-11-tetradecen-1-yl acetate, wherein the weight percentage of the maximum component in the communication disruptant is equal to a value obtained by multiplying the weight percentage of the maximum component in the sex pheromone by a number in the range of 2/100 to 50/100.

3 Claims, No Drawings

COMMUNICATION DISRUPTANT AND COMMUNICATION DISRUPTION METHOD

This application is a 371 of PCT/JP98/03973, filed on Ser. No. Sep. 4, 1998.

TECHNICAL FIELD

This invention relates to communication disruptants which interfere with the copulation of insect pests and thereby control the infestation of larvae, and more particularly to communication disruptants which are effective against insect pests of the family Tortricidae.

BACKGROUND ART

Generally, all components of a natural sex pheromone are frequently used in communication disruptants. However, in the case, for example, of communication disruptants for species belonging to the family Tortricidae and having (Z)-11-tetradecen-1-yl acetate as a component of their sex pheromone composition, (Z)-11-tetradecen-1-yl acetate alone has been used without regard to the other components of the sex pheromone of the species. The addition of other components has been said to bring about no improvement in effectiveness.

However, when a communication disruptant containing (Z)-11-tetradecen-1-yl acetate as the only active ingredient is continually used for a period of 5 to 10 years, a phenomenon has been observed in which its communication-disrupting effect on insect pests, particularly of the family Tortricidae, living in the field or the like through successive generations is reduced. Accordingly, it is eagerly desired to develop a new communication disruptant which is also effective for such fields where the communication-disrupting effect (on insect pests, particularly of the family Tortricidae, living there through successive generations) has been reduced.

DISCLOSURE OF INVENTION

As a result of extensive investigations on communication disruptants comprising (Z)-11-tetradecen-1-yl acetate and other sex pheromone components, the present inventors have now completed the present invention.

Thus, the present invention provides, for use in the control of insect pests having (Z)-11-tetradecen-1-yl acetate contained in their sex pheromone, a communication disruptant containing (Z)-11-tetradecen-1-yl acetate and the maximum component in the composition of the sex pheromone excepting (Z)-11-tetradecen-1-yl acetate, wherein the weight percentage of the maximum component in the communication disruptant is equal to a value obtained by multiplying the weight percentage of the maximum component in the sex pheromone by a number in the range of 0.02 to 0.5.

The communication disruptant of the present invention makes it possible to control target insect pests while omitting or decreasing the use of an insecticide therefor. Consequently, it has the great merit of being economically advantageous, yielding pesticide-restricted crops, and hence contributing to the securement of safety for human beings.

BEST MODE FOR CARRYING OUT THE INVENTION

The communication disruptant of the present invention contains both (Z)-11-tetradecen-1-yl acetate and the maximum component in the composition of the natural sex pheromone excepting (Z)-11-tetradecen-1-yl acetate. Preferably, the weight percentage of the maximum component in the communication disruptant is equal to a value obtained by multiplying the weight percentage of the maximum component in the natural sex pheromone by a number in the range of 0.02 to 0.5 and more preferably 0.02 to 0.3. If the number is less than 0.02, the resulting communication-disrupting effect will be insufficient, while if the number is greater than 0.5, the resulting communication-disrupting effect will be reduced contrariwise.

The maximum component excepting (Z)-11-tetradecen-1-yl acetate is defined as follows: Where the natural pheromone contains a plurality of components in addition to (Z)-11-tetradecen-1-yl acetate, the component having the highest weight percentage of all components but (Z)-11-tetradecen-1-yl acetate is the maximum component. Where the natural pheromone contains only one component in addition to (Z)-11-tetradecen-1-yl acetate, that component is the maximum component.

In the communication disruptant of the present invention, the maximum component preferably comprises (Z)-9-tetradecen-1-yl acetate, (Z)-9-dodecen-1-yl acetate or (E)-11-tetradecen-1-yl acetate.

The communication disruptant of the present invention is effective in disrupting the communication of insect pests of the family Tortricidae and, in particular, the subfamily Tortricinae. Specific and preferable examples of such insect pests include *Adoxophyes orana* (summer fruit tortrix), *Adoxophyes* sp. (smaller tea tortrix), *Pandemis limitata, Pandemis pyrusana, Pandemis heparana, Archips breviplicana* (Asiatic leafroller), *Archips fusscocupreana* (apple tortrix), *Archips podana, Argyrotaenia velutinana, Choristoneura rosaceana,* and *Homona magnamina* (oriental tea tortrix). More specifically, the communication disruptant of the present invention is particularly effective in disrupting the communication of insect pests of the family Tortricidae to fruit trees or tea trees, including the summer fruit tortrix which is an insect pest detrimental to apple, pear, peach, ume (Japanese apricot) and cherry trees, the Asiatic leafroller which is an insect pest detrimental to apple, pear and like trees, and the oriental tea tortrix and smaller tea tortrix which are insect pest detrimental to tea leaves.

The natural sex pheromone components and distribution of principal insect pests of the family Tortricidae are shown in Table 1, and the chemical formulae of those components are given below.

TABLE 1

Sex pheromone components and distribution of principal insect pests of the family Tortricidae

| Name of tortricid | Crop | Sex pheromone components (percentage) | Distribution |
|---|---|---|---|
| *Adoxophyes orana* (summer fruit tortrix) | Fruit trees | (Z)-9-tetradecen-1-yl acetate (90) (Z)-11-tetradecen-1-yl acetate (10) | Japan, Europe |
| *Archips breviplicana* (Asiatic leafroller) | Fruit trees | (Z)-11-tetradecen-1-yl acetate (30) (E)-11-tetradecen-1-yl acetate (70) | Japan |
| *Homona magnamina* (oriental tea tortrix) | Tea | (Z)-11-tetradecen-1-yl acetate (88) (Z)-9-dodecen-1-yl acetate (9) 11-dodecen-1-yl acetate (3) | Japan |

TABLE 1-continued

Sex pheromone components and distribution of principal insect pests of the family Tortricidae

| Name of tortricid | Crop | Sex pheromone components (percentage) | Distribution |
|---|---|---|---|
| Adoxophyes sp. (smaller tea tortrix) | Tea | (Z)-9-tetradecen-1-yl acetate (63)<br>(Z)-11-tetradecen-1-yl acetate (31)<br>(E)-11-tetradecen-1-yl acetate (4)<br>10-methyldodecyl acetate (2) | Japan |
| Archips fusscocupreana (apple tortrix) | Fruit trees | (Z)-11-tetradecen-1-yl acetate (80)<br>(E)-11-tetradecen-1-yl acetate (20) | Japan |
| Pandemis heparana (Pandemis leafroller) | Fruit trees | (Z)-9-tetradecen-1-yl acetate (5)<br>(Z)-11-tetradecen-1-yl acetate (90)<br>(Z)-11-tetradecen-1-yl alcohol (5) | Japan, Europe |
| Archips podana | Fruit trees | (Z)-11-tetradecen-1-yl acetate (50)<br>(E)-11-tetradecen-1-yl acetate (50) | Europe |
| Choristoneura rosaceana | Fruit trees | (Z)-11-tetradecen-1-yl acetate (98)<br>(E)-11-tetradecen-1-yl acetate (2) | North America |
| Pandemis limitata | Fruit trees | (Z)-9-tetradecen-1-yl acetate (9)<br>(Z)-11-tetradecen-1-yl acetate (91) | North America |
| Pandemis pyrusana | Fruit trees | (Z)-9-tetradecen-1-yl acetate (6)<br>(Z)-11-tetradecen-1-yl acetate (94) | North America |
| Argyrotaenia velutinana | Fruit trees | (Z)-11-tetradecen-1-yl acetate (88)<br>(E)-11-tetradecen-1-yl acetate (12) | North America |

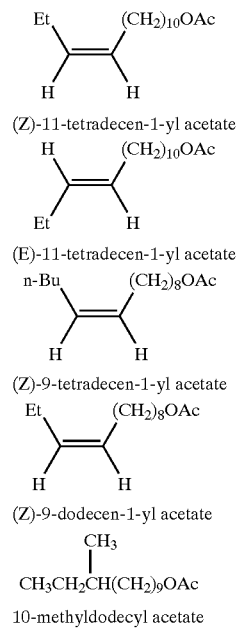

(Z)-11-tetradecen-1-yl acetate (E)-11-tetradecen-1-yl acetate (Z)-9-tetradecen-1-yl acetate (Z)-9-dodecen-1-yl acetate 10-methyldodecyl acetate The synthesis of various geometrical isomers used in the present invention, such as (Z)-11-tetradecen-1-yl acetate, (Z)-9-tetradecen-1-yl acetate, (Z)-9-dodecen-1-yl acetate, (E)-11-tetradecen-1-yl acetate and 10-methyldodecyl acetate, can be carried out according to conventionally known processes.

Moreover, in order to prevent oxidation or decomposition of the communication disruptant of the present invention, antioxidants or ultraviolet absorbers may be used therein as required.

Useful antioxidants include, for example, di-tert-butylhydroxytoluene (BHT), vitamin E and 2,5-di-tert-butylhydroquinone (DBH).

Useful ultraviolet absorbers include, for example, 2-(2'-hydroxy-3-tert-butyl-5-methylphenyl)-5-chlorobenzotriazole and 2-hydroxy-4-octoxybenzophenone (HOBP).

Antioxidants and ultraviolet absorbers may each be used in an amount of 0.1 to 5.0% by weight, preferably 1.0 to 3.0% by weight, based on the communication disruptant. If the amount is less than 0.1% by weight, the resulting communication disruptant will have poor stability and hence a short useful life. Even if the amount exceeds 5.0% by weight, no substantial difference in stability will be made.

In preparing the communication disruptant of the present invention, well-known polyethylene tubes are filled with a synthetic pheromone in an amount of 80 to 240 mg per tube according to a technique associated with small tubes for the controlled release of a pheromone (Japanese Patent Provisional Publication No. 57-9705/'82) and a technique for giving shape thereto (Japanese Patent Provisional Publication No. 57-156403/'82). The duration of its communication-disrupting effect generally ranges from 3 to 6 months, depending on such conditions as the configuration of the field to which it is applied.

The communication disruptant of the present invention is preferably applied in an amount of 50 to 500 tubes per 10 ares. This range may vary according to the area of application, weather conditions, conditions of location (e.g., the configuration of the field), and the form of the communication disruptant. For example, in the case of a field whose area is as large as 1 ha or more and where the velocity of wind is low, the number of tubes used may be slightly decreased.

The communication disruptant of the Resent invention is sealed in polyethylene tubes, so that it permeates through the wall of the tube, evaporates from the outer wall surface of the tube, and is thereby released slowly and persistently into the atmosphere (air) of the field.

EXAMPLES

The present invention is further illustrated by the following examples. However, these examples are not to be construed to limit the scope of the invention. As an antioxidant, 2% by weight of BHT was added to the communication disruptants used in Examples 1 to 9 and Comparative Examples 1 to 15. Moreover, as an ultraviolet absorber, 2% by weight of HOBP was added to the communication disruptants used in Examples 4 to 6 and Comparative Examples 6 to 10. Unless otherwise noted, the test fields used in the examples and comparative examples were sprayed with the same dose of an insecticide for insect pests of the family Tortricidae, and two insecticide-spraying operations were omitted from a conventional pest control scheme (usually consisting of six insecticide-spraying operations).

Examples 1 to 3 and Comparative Examples 1 to 5

Tests for the Evaluation of Effectiveness Against the Smaller Tea Tortrix

Synthetic pheromones were prepared by mixing (Z)-11-tetradecen-1-yl acetate and (Z)-9-tetradecen-1-yl acetate in a weight ratio of 100:0 (Comparative Examples 1 and 2), 98:2 (Example 1), 90:10 (Example 2), 80:20 (Example 3) or 33:67 (natural composition; Comparative Examples 3 and 4), and 160 mg each of these synthetic pheromones were sealed into polyethylene tubes having a length of 20 cm to produce communication disruptants. Each of the communication disruptants was uniformly applied, in an amount of 5,000 tubes/ha or 15,000 tubes/ha, to a tea garden (with an area of 1 ha) where a commercially available (Z)-11-tetradecen-1-yl acetate preparation (comprising (Z)-11-tetradecen-1-yl acetate alone) had been continually used for the past 5 to 15 years. In the central region of this tea garden, two pheromone traps for the smaller tea tortrix and one blank trap were placed at intervals of 5 m, and the number of moths (of the smaller tea tortrix) lured into each trap was examined through generations. Moreover, a conventionally pest-controlled tea garden (i.e., a tea garden where pest control was performed with an ordinary insecticide alone) located about 100 m away therefrom was employed as a control plot (a pheromone-untreated plot; Comparative Example 5). In this control plot, two pheromone traps and one blank trap were placed in the same manner as in the tea gardens treated with the communication disruptants, and the number of moths lured into each trap was examined. The degree of communication disruption was calculated according to the following equation.

Degree of communication disruption (%)=100-{(Number of moths lured into the pheromone traps of the treated tea garden)×100/ (Number of moths lured into the pheromone traps of the untreated tea garden)}

In the above equation, the number of moths lured into the pheromone traps of the treated tea garden and the untreated tea garden were corrected by subtracting therefrom the number of moths caught in the blank traps during the same period of time.

Moreover, in order to evaluate the pest control effect of the communication disruptants of the present invention, the number of larvae found in each tea garden was examined. The pest control effect was expressed in terms of the number of tortricid larvae per unit area of the tea garden or the like. In the case of a fruit garden, a number of test fruit trees were sampled, 20 current shoots of each tree were examined, and the degree of damage to current shoots was calculated from the number of current shoot having a broken core. The communication-disrupting and pest-controlling effects of various communication disruptants on the smaller tea tortrix are shown in Table 2.

TABLE 2

Communication-disrupting effect and pest control effect (number of larvae) of various communication disruptants on the smaller tea tortrix

| | Composition of communication disruptant (weight ratio) Z11:Z9* | Area of treated plot (ha) | Number of tubes treated (tubes/ ha) | Degree of communi- cation disruption (%) | Number of larvae (larvae/m$^2$) |
|---|---|---|---|---|---|
| Example 1 | 98:2 | 1 | 5,000 | 100 | 0.1 |
| Example 2 | 90:10 | 1 | 5,000 | 99 | 0.1 |
| Example 3 | 80:20 | 1 | 5,000 | 98 | 0.4 |
| Com.Ex. 1 | 100:0 | 1 | 5,000 | 65 | 4.2 |
| Com.Ex. 2 | 100:0 | 1 | 15,000 | 87 | 3.4 |
| Com.Ex. 3 | 33:67 | 1 | 5,000 | 99 | 1.6 |
| Com.Ex. 4 | 33:67 | 1 | 15,000 | 100 | 0.2 |
| Com.Ex. 5 | None | 0.1 | — | — | 4.3 |

*Z11 designates (Z)-11-tetradecen-1-yl acetate and Z9 designates (Z)-9-tetradecen-1-yl acetate.

It can be seen from Table 2 that, in tea gardens where a commercially available (Z)-11-tetradecen-1-yl acetate preparation had been continually used for 5 to 15 years, the treatment with (Z)-11-tetradecen-1-yl acetate alone (comparative Examples 1 and 2) produced little communication-disrupting or pest-controlling effect. However, when the communication disruptants of the present invention were used, a degree of communication disruption of 98% or greater was achieved and a high pest control effect represented by at most 0.4 larva per square meter was obtained. On the other hand, when the pheromone having the natural composition was used as a communication disruptant in the same amount (i.e. the same number of tubes) as the communication disruptants of the present invention, the degree of communication disruption was satisfactory, but its pest control effect was poor. Its amount required to produce an equal pest control effect was three times as large as that of the communication disruptants of the present invention (Comparative Example 4).

Examples 4 to 6 and Comparative Examples 6 to 10

Tests for the Evaluation of Effectiveness Against the Oriental Tea Tortrix

Synthetic pheromones were prepared by mixing (Z)-11-tetradecen-1-yl acetate and (Z)-9-dodecen-1-yl acetate in a weight ratio of 100:0 (Comparative Examples 6 and 7), 99.6:0.4 (Example 4), 98.6:1.4 (Example 5), 97.3:2.7 (Example 6) or 90.7:9.3 (natural composition; Comparative Examples 8 and 9), and 160 mg each of these synthetic pheromones were sealed into polyethylene tubes having a length of 20 cm to produce communication disruptants. Each of the communication disruptants was uniformly applied, in an amount of 5,000 tubes/ha or 15,000 tubes/ha, to a tea garden (with an area of 1 ha) where a commercially available (Z)-11-tetradecen-1-yl acetate preparation had been continually used for the past 5 to 15 years. In the central region of this tea garden, two pheromone traps for the oriental tea tortrix and one blank trap were placed at intervals of 5 m, and the number of moths (of the oriental tea tortrix) lured into each trap was examined through generations. Moreover, a conventionally pest-controlled tea garden located about 100 m away therefrom was employed as an untreated control plot (a pheromone-untreated plot; Comparative Example 10). In this control plot, two pheromone traps and one blank trap were placed in the same manner as in the tea gardens treated with the communication disruptants. The communication-disrupting and pest-controlling effects of various communication disruptants on the oriental tea tortrix were tested in the same manner as described above, and are shown in Table 3.

TABLE 3

Communication-disrupting effect and pest control effect (number of larvae) of various communication disruptants on the oriental tea tortrix

| | Composition of communication disruptant (weight ratio) Z11:Z9* | Area of treated plot (ha) | Number of tubes treated (tubes/ ha) | Degree of communi- cation disruption (%) | Degree of damage to current shoots (larvae/ m$^2$) |
|---|---|---|---|---|---|
| Example 4 | 99.6:0.4 | 1 | 5,000 | 98 | 0.1 |
| Example 5 | 98.6:1.4 | 1 | 5,000 | 97 | 0.1 |
| Example 6 | 97.3:2.7 | 1 | 5,000 | 98 | 0.2 |
| Com.Ex. 6 | 100.0:0.0 | 1 | 5,000 | 55 | 5.3 |
| Com.Ex. 7 | 100.0:0.0 | 1 | 15,000 | 84 | 3.1 |

TABLE 3-continued

Communication-disrupting effect and pest control effect (number of larvae) of various communication disruptants on the oriental tea tortrix

| | Composition of communication disruptant (weight ratio) Z11:Z9* | Area of treated plot (ha) | Number of tubes treated (tubes/ha) | Degree of communication disruption (%) | Degree of damage to current shoots (larvae/m²) |
|---|---|---|---|---|---|
| Com.Ex. 8 | 90.7:9.3 | 1 | 5,000 | 99 | 0.5 |
| Com.Ex. 9 | 90.7:9.3 | 1 | 15,000 | 100 | 0.1 |
| Com.Ex. 10 | None | 0.1 | — | — | 7.9 |

*Z11 designates (Z)-11-tetradecen-1-yl acetate and Z9 designates (Z)-9-dodecen-1-yl acetate.

It can be seen from Table 3 that, in tea gardens where a (Z)-11-tetradecen-1-yl acetate preparation had been continually used for 5 to 15 years, the treatment with (Z)-11-tetradecen-1-yl acetate alone (comparative Examples 6 and 7) produced very little communication-disrupting or pest-controlling effect. However, when the communication disruptants of the present invention were used, a degree of communication disruption of 98% or greater was achieved and a high pest control effect represented by at most 0.2 larva per square meter was obtained. On the other hand, when the pheromone having the natural composition was used as a communication disruptant in the same amount as in the examples, its pest control effect was poor. Its amount required to produce an equal pest control effect was three times as large as that of the communication disruptants of the present invention (Comparative Example 9).

Examples 7 to 9 and Comparative Examples 11 to 15

Tests for the Evaluation of Effectiveness Against the Summer Fruit Tortrix

Synthetic pheromones were prepared by mixing (Z)-11-tetradecen-1-yl acetate and (Z)-9-tetradecen-1-yl acetate in a weight ratio of 100:0 (Comparative Examples 11 and 12), 97:3 (Example 7), 87:13 (Example 8), 73:27 (Example 9) or 10:90 (natural composition; Comparative Examples 13 and 14), and 80 mg each of these synthetic pheromones were sealed into polyethylene tubes having a length of 20 cm to produce communication disruptants. Each of the communication disruptants was uniformly applied, in an amount of 1,500 tubes/ha or 4,500 tubes/ha, to an apple orchard (with an area of 1 ha) where a commercially available (Z)-11-tetradecen-1-yl acetate preparation had been continually used for the past 5 to 10 years. In the central region of this apple orchard, two pheromone traps and one blank trap were placed at intervals of 5 m, and the number of moths lured into each trap was examined through generations. Moreover, a conventionally pest-controlled apple orchard located about 100 m away therefrom was employed as an untreated control plot (a plot not treated with any communication disruptant; Comparative Example 15). In this control plot, two pheromone traps and one blank trap were placed in the same manner as in the apple orchards treated with the communication disruptants. The degree of communication disruption was evaluated in the same manner as described previously. The pest control effect was evaluated in terms of the degree of damage to current shoots which was calculated according to the following equation.

Degree of damage to current shoots (%)=100-{(Number of current shoots damaged)/(Number of current shoots examined)}×100

The communication-disrupting and pest control effects of various communication disruptants on the summer fruit tortrix are shown in Table 4.

TABLE 4

Communication-disrupting effect and pest control effect (degree of damage to current shoots) of various communication disruptants on the summer fruit tortrix

| | Composition of communication disruptant (weight ratio) Z11:Z9* | Area of treated plot (ha) | Number of tubes treated (tubes/ha) | Degree of communication disruption (%) | Degree of damage to current shoots (%) |
|---|---|---|---|---|---|
| Example 7 | 97:3 | 1 | 1,500 | 100 | 0.1 |
| Example 8 | 87:13 | 1 | 1,500 | 100 | 0.1 |
| Example 9 | 73:27 | 1 | 1,500 | 99 | 0.2 |
| Com.Ex. 11 | 100:0 | 1 | 1,500 | 87 | 1.7 |
| Com.Ex. 12 | 100:0 | 1 | 4,500 | 92 | 1.2 |
| Com.Ex. 13 | 10:90 | 1 | 1,500 | 97 | 0.8 |
| Com.Ex. 14 | 10:90 | 1 | 4,500 | 99 | 0.1 |
| Com.Ex. 15 | None | 0.1 | — | — | 2.9 |

*Z11 designates (Z)-11-tetradecen-1-yl acetate and Z9 designates (Z)-9-tetradecen-1-yl acetate.

It can be seen from Table 4 that, in apple orchards where a (Z)-11-tetradecen-1-yl acetate preparation had been continually used for 5 to 10 years, the treatment with (Z)-11-tetradecen-1-yl acetate alone (comparative Examples 11 and 12) produced little communication-disrupting or pest-controlling effect. However, when the communication disruptants of the present invention were used, a degree of communication disruption of 100% or so was achieved in all cases and a high pest control effect represented by a degree of damage to current shoots of 0.1% was obtained. On the other hand, when the pheromone having the natural composition was used as a communication disruptant in the same amount as in the examples, no pest control effect was obtained. Its amount required to produce an equal pest control effect was three times as large as that of the communication disruptants of the present invention (Comparative Example 14).

Examples 10 to 12 and Comparative Examples 16 to 20

Tests for the Evaluation of Effectiveness Against the Asiatic Leafroller

Synthetic pheromones were prepared by mixing (Z)-11-tetradecen-1-yl acetate and (E)-11-tetradecen-1-yl acetate in a weight ratio of 100:0 (Comparative Examples 16 and 17), 98:2 (Example 10), 90:10 (Example 11), 79:21 (Example 12) or 30:70 (natural composition; Comparative Examples 18 and 19), and 80 mg each of these synthetic pheromones were sealed into polyethylene tubes having a length of 20 cm to produce communication disruptants. Each of the communication disruptants was uniformly applied to an apple orchard (with an area of 1 ha) in an amount of 1,500 tubes/ha or 4,500 tubes/ha. In the central region of this apple orchard, two pheromone traps and one blank trap were placed at intervals of 5 m, and the number of moths lured into each trap was examined through generations. Moreover, a conventionally pest-controlled apple orchard located about 100 m away therefrom was employed as an untreated control plot (a plot not treated with any communication disruptant; Comparative Example 20). In this control plot, two pheromone traps and one blank trap were placed in the same manner as in the apple orchards treated with the communication disruptants. The degree of communication disruption was evaluated in the same manner as described previously, and the pest control effect was evaluated in terms of the degree of damage to current shoots which was calculated in the above-described manner. The communication-disrupting and pest-controlling effects of various communication disruptants on the Asiatic leafroller are shown in Table 5.

TABLE 5

Communication-disrupting effect and pest control effect (degree of damage to current shoots) of various communication disruptants on the Asiatic leafroller

| | Composition of communication disruptant (weight ratio) Z11:E11* | Area of treated plot (ha) | Number of tubes treated (tubes/ ha) | Degree of communication disruption (%) | Degree of damage to current shoots (%) |
|---|---|---|---|---|---|
| Example 10 | 98:2 | 1 | 1,500 | 100 | 0.1 |
| Example 11 | 90:10 | 1 | 1,500 | 100 | 0.0 |
| Example 12 | 79:21 | 1 | 1,500 | 100 | 0.1 |
| Com.Ex. 16 | 100:0 | 1 | 1,500 | 94 | 2.4 |
| Com.Ex. 17 | 100:0 | 1 | 4,500 | 95 | 1.8 |
| Com.Ex. 18 | 30:70 | 1 | 1,500 | 98 | 1.3 |
| Com.Ex. 19 | 30:70 | 1 | 4,500 | 100 | 0.2 |
| Com.Ex. 20 | None | 0.1 | — | — | 2.9 |

*Z11 designates (Z)-11-tetradecen-1-yl acetate and E11 designates (E)-11-tetradecen-1-yl acetate.

It can be seen from Table 5 that, in apple orchards where a (Z)-11-tetradecen-1-yl acetate preparation had been continually used for 5 to 10 years, the treatment with (Z)-11-tetradecen-1-yl acetate alone (comparative Examples 16 and 17) produced little communication-disrupting or pest-controlling effect. However, when the communication disruptants of the present invention were used, a degree of communication disruption of 100% or so was achieved in all cases and a high pest control effect represented by a degree of damage to current shoots of 0.1% or less was obtained. On the other hand, when the pheromone having the natural composition was used as a communication disruptant in the same amount as in the examples, no pest control effect was obtained. Its amount required to produce an equal pest control effect was three times as large as that of the communication disruptants of the present invention (Comparative Example 19).

INDUSTRIAL APPLICABILITY

By using the communication disruptants of the present invention, powerful communication-disrupting and pest-controlling effects on insect pests having (Z)-11-tetradecen-1-yl acetate as a sex pheromone component can be stably and persistently obtained over a long period of time. Moreover, since the communication disruptants of the present invention can control target insect pests while omitting or decreasing the use of an insecticide therefor, they have an economic advantage, yield pesticide-restricted crops, and hence contribute to the securement of safety for human beings.

What is claimed is:

1. A method for the control of an insect pest of the family Tortricidae comprising the steps of:
    identifying the insect pest to be controlled, wherein the natural sex pheromone of said insect pest contains (Z)-11-tetradecen-1-yl acetate;
    obtaining a communication disruptant composition consisting essentially of (Z)-11-tetradecen-1-yl acetate and a second component found in the natural sex pheromone of said insect pest, wherein said second component is the component found in highest concentration in the natural sex pheromone other than (Z)-11-tetradecen-1-yl acetate, and further wherein the weight percentage of said second component in the communication disruptant composition is equal to a value obtained by multiplying the weight percentage of said second component in the natural sex pheromone by a number in the range of 0.02 to 0.5; and,
    exposing said insect pest to said communication disruptant;
    wherein the second component is (Z)-9-tetradecen-1-yl acetate and wherein said insect pest is a member of the group consisting of Adoxophyes sp. (smaller tea tortrix), *Pandemis limitata*, and *Pandemis pyrusana*.

2. A method for the control of an insect pest of the family Tortricidae comprising the steps of:
    identifying the insect pest to be controlled, wherein the natural sex pheromone of said insect pest contains (Z)-11-tetradecen-1-yl acetate;
    obtaining a communication disruptant composition consisting essentially of (Z)-11-tetradecen-1-yl acetate and a second component found in the natural sex pheromone of said insect pest, wherein said second component is the component found in highest concentration in the natural sex pheromone other than (Z)-11-tetradecen-1-yl acetate, and further wherein the weight percentage of said second component in the communication disruptant composition is equal to a value obtained by multiplying the weight percentage of said second component in the natural sex pheromone by a number in the range of about 0.14 to 0.5 wherein the second component is (E)-11-tetradecen-1-yl acetate and said insect pest is *Archips breviplicana*; and,
    exposing said insect pest to said communication disruptant.

3. A method for the control of an insect pest of the family Tortricidae comprising the steps of:
    identifying the insect pest to be controlled, wherein the natural sex pheromone of said insect pest contains (Z)-11-tetradecen-1-yl acetate;
    obtaining a communication disruptant composition consisting essentially of (Z)-11-tetradecen-1-yl acetate and a second component found in the natural sex pheromone of said insect pest, wherein said second component is the component found in highest concentration in the natural sex pheromone other than (Z)-11-tetradecen-1-yl acetate, and further wherein the weight percentage of said second component in the communication disruptant composition is equal to a value obtained by multiplying the weight percentage of said second component in the natural sex pheromone by a number in the range of 0.02 to 0.5; and,
    exposing said insect pest to said communication disruptant;
    wherein the second component is (E)-11-tetradecen-1-yl acetate and said insect pest is a member of the group consisting of *Archips podana, Choristoneura rosaceana* and *Argyrotaenia velutinana*.

* * * * *